US00PP16016P3

(12) United States Plant Patent
Laviana

(10) Patent No.: US PP16,016 P3
(45) Date of Patent: Oct. 4, 2005

(54) ***COREOPSIS* PLANT NAMED 'HEAVEN'S GATE'**

(50) Latin Name: *Coreopsis rosea*
Varietal Denomination: Heaven's Gate

(75) Inventor: Marc R. Laviana, Kensington, CT (US)

(73) Assignee: Sunny Border Nurseries, Inc., Kensington, CT (US)

( * ) Notice: Subject to any disclaimer, the term of this patent is extended or adjusted under 35 U.S.C. 154(b) by 6 days.

(21) Appl. No.: 10/761,446

(22) Filed: Jan. 20, 2004

(65) Prior Publication Data

US 2005/0160510 P1 Jul. 21, 2005

(51) Int. Cl.[7] ..... A01H 5/00
(52) U.S. Cl. ..... Plt./263
(58) Field of Search ..... Plt./263

*Primary Examiner*—Kent L. Bell
(74) *Attorney, Agent, or Firm*—Penny J. Aguirre

(57) ABSTRACT

A new cultivar of *Coreopsis rosea* 'Heaven's Gate' characterized by an unique inflorescence coloration of purple ray florets ranging from bi-colors with a basal region that is deep purple and the more distal regions a lighter purple to deep purple throughout the floret with no bi-color effect exhibited.

1 Drawing Sheet

Botanical classification: *Coreopsis rosea.*
Variety denomination: 'Heaven's Gate'.

BACKGROUND OF THE INVENTION

The present invention relates to a new and distinct cultivar of *Coreopsis* plant, botanically known as *Coreopsis rosea* 'Heaven's Gate' and will be referred to hereinafter by its cultivar name 'Heaven's Gate'. The new cultivar of *Coreopsis* is an herbaceous perennial growth for landscape and container use.

The inventor discovered the new cultivar, 'Heaven's Gate', in a block of nursery containers of *Coreopsis rosea* 'Sweet Dreams' (U.S. Plant Pat. No. 12,720) in Kensington, Conn. in the summer of 2002. The inventor presumes that the new cultivar was derived as a naturally occurring branch mutation of 'Sweet Dreams', as the plants were grown from plugs of 'Sweet Dreams' that were presumably produced from stem cuttings.

'Heaven's Gate' was selected based on the coloration of its ray florets. The ray florets of 'Heaven's Gate' exhibit an increased in the amount of purple coloration resulting in deeper colored flowers and a less pronounced bi-color effect in comparison to 'Sweet Dreams'. Other characteristics of 'Heaven's Gate' are similar to 'Sweet Dreams' therefore distinguishing it as well from the parent of 'Sweet Dreams', 'American Dreams' (unpatented). These characteristics make this new cultivar unique and unlike any other known cultivars of *Coreopsis rosea* known to the inventor.

Asexual reproduction of the new cultivar was first accomplished by terminal stem cuttings in a controlled environment in Kensington, Conn. in summer of 2002 by the inventor. The characteristics of this cultivar have been determined to be stable and are reproduced true to type in successive generations.

SUMMARY OF THE INVENTION

The following traits have been repeatedly observed and are determined to be the characteristics of the new cultivar. These attributes in combination distinguish 'Heaven's Gate' as unique from 'Sweet Dreams' and all other varieties of *Coreopsis* known to the inventor.

1. Composite inflorescences ranging from 3 to 4 cm in diameter.
2. Unique purple ray florets ranging from bi-colors with a basal region that is deep purple and the more distal regions a lighter purple to deep purple throughout the floret with no bi-color effect exhibited.
3. Free flowering with numerous inflorescences. Naturally blooms from late spring until frost.
4. Upright and outwardly spreading growth habit and freely branched.

BRIEF DESCRIPTION OF THE DRAWING

The accompanying colored photographs illustrate the overall appearance and distinct characteristics of the new *Coreopsis.*

The photograph on the top of the sheet is a view of a typical plant of 'Heaven's Gate' in bloom as grown in a one-gallon container.

The photograph on the bottom of the sheet is of a composite of flowers removed from plants of 'Heaven's Gate' (top row) and 'Sweet Dreams' (bottom row).

The flowers were obtained from plants grown in one-gallon under similar cultural conditions. The colors in the photographs are as close as possible with the photographic and printing technology utilized. The color values cited in the detailed botanical description accurately describe the colors of the new *Coreopsis.*

DETAILED BOTANICAL DESCRIPTION

The following is a detailed description of the new cultivar as grown outdoors in one-gallon containers. The plants were 8 to 9 months in age. The phenotype of the new cultivar may vary with variations in environmental, climatic, and cultural conditions, as it has not been tested under all possible environmental conditions. The color determination is in accordance with the 1995 R.H.S. Colour Chart of The Royal Horticultural Society, London, England, except where general color terms of ordinary dictionary significance are used.

Botanical classification: 'Heaven's Gate' is a cultivar of *Coreopsis rosea*.

Common name: Tickseed.

Parentage: Naturally occurring stem branch mutation of *Coreopsis rosea* 'Sweet Dreams'.

General description:

*Blooming period.*—Under natural conditions, blooms from late spring until frost in fall.

*Plant habit.*—Herbaceous perennial. Upward habit, vegetative foliage spreading outward.

*Height and spread.*—Up to 35 cm width and up to about 50 cm height.

*Hardiness.*—Zone 6, had not been tested in colder zones.

*Culture.*—Tolerant to a wide range of growing conditions, growing well in full sun to light shade, in dry to moist soils if well-drained. Performs well in containers.

*Diseases and pests.*—No susceptibility or resistance to diseases or pests has been observed for 'Heaven's Gate'.

*Root description.*—Fibrous, fine and well-branched.

Growth and propagation:

*Propagation.*—Terminal stem cuttings.

*Root initiation.*—7 to 10 days at about 25° to 30° C. air temp in spring and summer.

*Time required for root development.*—8 weeks to fully develop in a 32 cell in soil-less media when grown at 25° to 30° C. in a greenhouse without supplemental lighting in summer.

*Growth rate.*—Moderate to vigorous.

Stem description:

*Shape.*—Round, solid.

*Stem color.*—Medium green, 146A.

*Stem size.*—About 1 to 2 mm in diameter and 35 to 50 cm in length.

*Stem surface.*—Glabrous.

*Branching habit.*—Very freely branched, typically branching as two opposite laterals at each node. Aspect is upward then outward when in bloom. Pinching is not required for branching.

Foliage description:

*Leaf division.*—Typically dissected into two or three segments, segment margins are entire.

*Leaflet shape.*—Linear.

*Leaf base.*—Attenuate.

*Leaf apex.*—Acute.

*Leaf venation.*—Only midrib is visible, not conspicuous, coloration same as leaf.

*Leaf attachment.*—Sessile.

*Leaf arrangement.*—Opposite.

*Leaf surface.*—Glabrous, upper and lower surfaces.

*Leaf color.*—Young: upper 147A, lower 146A. Mature: upper 147A, lower 146A.

*Leaf size.*—4 to 6 cm in length, about 3 cm in width when trifid. Leaf segments are about 2 to 4 cm in length and1 to 3 mm in width. Center segment is longer than laterals.

Flower description:

General description:

*Type.*—Capitulum: heterogamous with ray florets around the head margin and disc florets in the center, forming a radiant head. Inflorescences are borne on terminals arising from leaf axils.

*Lastingness of inflorescence.*—About one week until senescence of ray florets. Bracts and disc flowers are persistent.

*Fragrance.*—Moderate, sweet.

*Quantity of inflorescences.*—Very free flowering, over 100 per plant grown in a one-gallon container.

*Inflorescence size.*—About 9 mm in depth and 2.8 to 4.0 cm in diameter.

*Inflorescence buds.*—About 4.5 mm in height and diameter, shape is spherical, color changes with development from 199A (green) to 173A (grayed orange) to N77 (purple).

*Peduncle.*—Strong, wiry, about 2 to 6 cm in length and about 1 mm in diameter, 146A in color, texture is glabrous.

Phyllaries:

*Number.*—About 8 arranged in two rows, an inner and outer row.

*Size.*—Inner phyllaries; 3 mm in depth and 1.5 mm in width, outer phyllaries; about 6.5 mm in length and 3 mm in width.

*Color (both surfaces).*—Inner phyllaries; 146A, outer phyllaries; 148A (base), 163C (mid region), 163A (apex).

*Texture.*—Glabrous, waxy.

*Apex.*—Acute.

*Shape.*—Ovate.

*Margin.*—Entire.

*Base.*—Rounded.

Ray florets:

*Number.*—8.

*Shape.*—Roughly obovate, appearance of three longitudinal sections on lighter colored florets.

*Size.*—1.3 to 1.7 mm in length and 0.7 to 1 mm in width.

*Apex.*—Emarginate with 3 notches.

*Base.*—Attenuate.

*Margins.*—Entire.

*Aspect.*—Flat, held upright and up to a 45° from the peduncle.

*Texture.*—Glabrous.

*Color.*—Upper: when opening and fully open, base (eye) is N79C (deep purple), center and apex range from 76D with an overlay of N81C (appears light violet with a deeper colored eye) to a center and apex of N81C (appears medium pink with a deeper colored eye) to a center and apex of N79C with little visible distinction of the eye (not bi-colored). When eye is visible, it generally extends about 3 to 5 mm from the point of ray floret attachment. On the medium pink florets, longitudinal lines of N79C frequently extend from eye region. Lower: when opening and fully open, ranges from 76C on the lighter colored blooms to 76A. Lower surface of darkest florets are 76A with an overlay of N79C.

Disc florets:

*Quantity of florets.*—Numerous, greater than 100.

*Arrangement.*—Densely packed in center of inflorescence.

*Shape.*—Tubular, corolla is fused, flared at apex.

*Size.*—About 6 mm in length and 1 mm in width at apex, 0.5 mm at base.

*Color.*—Base (tube) is 16C in color, flared portion is 16C and translucent, apex is 163A.

*Diameter of entire disc.*—0.7 to 1.2 cm.

Reproductive organs:

*Presence.*—Disc florets are perfect, ray florets appear to be sterile.

*Gynoecium (present on disc florets only).*—1 Pistil, 6 mm in length, 3 mm in width and 16C in color, bifid stigma is 16A in color, 0.5 mm in height, 3 mm in length, showy. Ovary is 1 mm in length, 0.5 mm in width, placement is inferior, translucent in color.

*Androecium* (*present on disc florets only*).—5 stamens, fused into tube surrounding style, 1 mm in length and 0.5 mm in width, 202A in color (black), pollen is scarcely abundant and 15A in color.

*Fruit*.—An achene, flattened, winged, 1.5 mm in length, 0.3 mm in width, N199D in color. Viability has not been tested.

What is claimed:

1. A new and distinct cultivar of *Coreopsis* plant named 'Heaven's Gate' as herein illustrated and described.

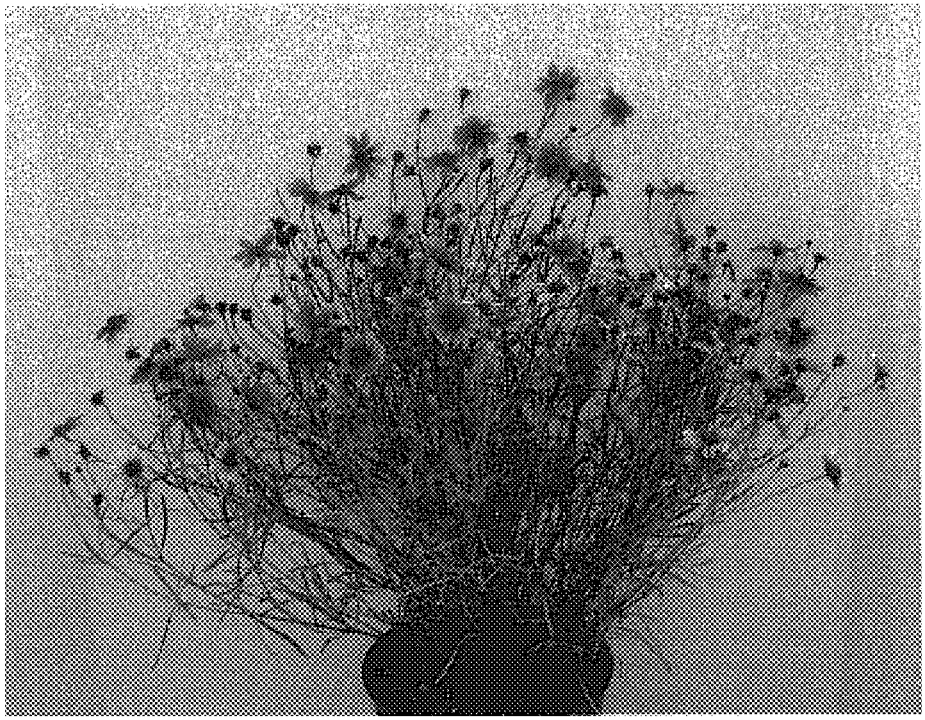
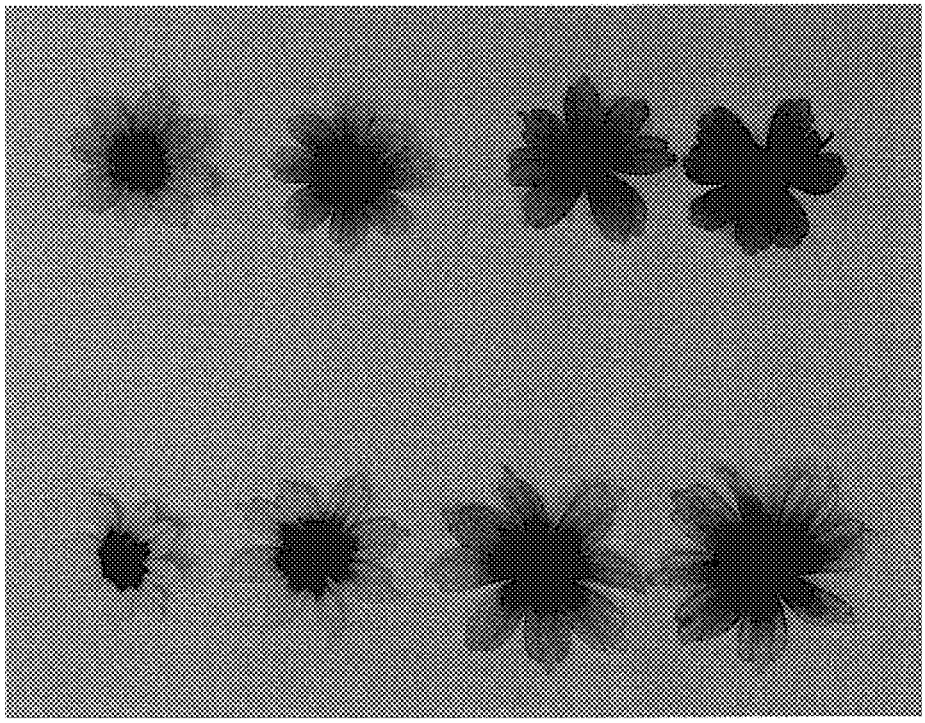

* * * * *